(12) United States Patent
Pasricha

(10) Patent No.: US 8,273,729 B2
(45) Date of Patent: *Sep. 25, 2012

(54) TREATMENT OF IRRITABLE BOWEL SYNDROME AND RELATED BOWEL DISEASE

(75) Inventor: Pankaj J. Pasricha, Cupertino, CA (US)

(73) Assignee: The Board Of Regents Of The University of Texas System, Austin, TX (US)

( * ) Notice: Subject to any disclaimer, the term of this patent is extended or adjusted under 35 U.S.C. 154(b) by 156 days.

This patent is subject to a terminal disclaimer.

(21) Appl. No.: 12/798,455

(22) Filed: Apr. 5, 2010

(65) Prior Publication Data

US 2010/0197648 A1 Aug. 5, 2010

Related U.S. Application Data

(62) Division of application No. 10/665,770, filed on Sep. 19, 2003, now Pat. No. 7,704,985.

(51) Int. Cl.
*A61K 31/56* (2006.01)

(52) U.S. Cl. .................................................. 514/179
(58) Field of Classification Search .................. 514/179
See application file for complete search history.

(56) References Cited

U.S. PATENT DOCUMENTS 7,704,985 B2 * 4/2010 Pasricha ...................... 514/179

* cited by examiner

*Primary Examiner* — Jennifer M Kim

(57) ABSTRACT

The present invention discloses a method of treating an individual having irritable bowel syndrome or a related disorder, comprising the step of administering to said individual a pharmacologically effective dose of a luminally active anti-inflammatory or immunosuppressive compound with minimal or no systemic side effects. Further provided is a method of inhibiting the onset of symptoms of irritable bowel syndrome or a related disorder in an individual in need of such treatment, comprising the step of administering to the individual a prophylactically effective dose of a luminally active anti-inflammatory or immunosuppressive compound with minimal or no systemic side effects.

3 Claims, 2 Drawing Sheets

TREATMENT OF IRRITABLE BOWEL SYNDROME AND RELATED BOWEL DISEASE

CROSS-REFERENCE TO RELATED APPLICATION

This divisional application claims benefit of priority under 35 U.S.C. §120 of nonprovisional application U.S. Ser. No. 10/665,770, filed Sep. 19, 2003 now U.S. Pat. No.7,704,985, which claims benefit of priority under 35 U.S.C. §119(e) of provisional application U.S. Ser. No. 60/412,234, filed Sep. 20, 2002, the entirety of both of which are hereby incorporated by reference.

BACKGROUND OF THE INVENTION

1. Field of the Invention

The present invention relates generally to the pharmacology and medical therapeutics of irritable bowel syndrome and related bowel diseases. More specifically, the present invention relates to the uses of luminally active anti-inflammatory or immunosuppressive compounds with minimal or no systemic side effects, for treatment of irritable bowel syndrome and related disorders.

2. Description of the Related Art

Irritable Bowel Syndrome is characterized, in part, by painful defecation and altered stool frequency/consistency and has a reported prevalence between 15-25% in both the industrialized and developing world (1). Irritable Bowel Syndrome, unlike most other diseases of the gastrointestinal tract, is not characterized by any specific, currently known histopathological changes, but rather is a functional disorder characterized, in part, by disturbed gut motility and/or abdominal pain perception linked to cytokines and/or other inflammatory cascades (2). Irritable Bowel Syndrome also occurs in Inflammatory Bowel Disease (IBD) patients who are in remission from their symptoms (3).

The precise pathophysiology of irritable bowel syndrome is not well understood. Nevertheless, there is a heightened sensitivity to visceral pain perception in irritable bowel syndrome, known as "peripheral sensitization". This sensitization involves a reduction in the threshold and an increase in the gain of the transduction processes of primary afferent neurons, attributable to a variety of mediators including monoamines (both catecholamines and indoleamines), substance P, and variety of cytokines and prostanoids including the E-type prostaglandins (4). Also implicated in the etiopathology of irritable bowel syndrome is intestinal motor dysfunction (gut dysmotility) which leads to abnormal handling of intraluminal contents and/or gas (5-6). Psychological factors may also contribute to irritable bowel syndrome symptoms appearing in conjunction with, if not triggered by, disturbances including depression and anxiety (7).

Although the etiology of irritable bowel syndrome is not fully characterized, validated diagnostic schemata for irritable bowel syndrome are available. For example, the Rome criteria and the Manning criteria allow the diagnosis of irritable bowel syndrome to be made based upon patient history. As an example, the Rome criteria requires three months of continuous or recurrent abdominal pain or discomfort that is relieved by defecation and/or associated with a change in stool frequency or consistency as well as two or more of the following: altered stool frequency, altered stool form, altered stool passage, passage of mucus, or bloating and abdominal distention. The absence of any structural or biochemical disorders that could be causing the symptoms is also a necessary condition.

Irritable bowel syndrome represents a therapeutic challenge to both clinicians and developers of pharmaceuticals. The uncertainty and variety of causes, as well as the variable nature of symptomatic expression greatly complicates the task of treating this disorder. As noted above, irritable bowel syndrome is a functional bowel disorder that is characterized by, for example, abdominal pain and/or discomfort in association with abnormal stool frequency and/or consistency, for example, diarrhea or constipation.

The earliest and most simple treatments have focused on symptomatic relief. For diarrhea-predominant irritable bowel syndrome, anti-diarrheal agents such as loperamide and diphenoxylate have been used with some success, especially in acute, situation-specific settings (8). Dietary supplementation with fiber or psyllium products has typically been recommended to irritable bowel syndrome patients, particularly those with constipation-predominant symptoms. More recent studies, however have cast some doubt on the real benefit provided by this strategy (9-10).

More aggressive treatments for constipation-predominant symptoms include lactulose, docusate, and prokinetic agents such as cisapride (11). Symptomatic relief of the pain associated with irritable bowel syndrome has been attempted with a variety of smooth muscle relaxants/antispasmodics as well as anticholinergic agents. Meta-analyses of these studies indicate an efficacy greater than placebo for five agents: cimetropium bromide (antimuscarinic), primaverium/octolinium bromide (calcium antagonists), tremebutine (peripheral opiate antagonist), and mebeverine (anticholinergic) (12-13).

There are a number of prokinetic agents that have been examined in the treatment of irritable, bowel syndrome. Such investigational prokinetic agents include nitric oxide synthase inhibitors, adrenoceptor antagonists, gonadotropin-releasing hormone (GnRH) analogues such as leuprolide, cholecystokinin-a (CCK.sub.A) antagonists, and certain opioid receptor antagonists (14-18). Adrenergic beta.sub.3 selective agonists have also been examined as potential antispasmodic/smooth muscle relaxant (19).

Many newer treatments also focus on targets, both peripheral and central, that are implicated in contributing to the cause and progression of irritable bowel syndrome. As mentioned above, visceral hyperalgesia (characterized by an abnormally low pain threshold in GI afferent sensory neurons) has been implicated in irritable bowel syndrome etiopathology. The role of serotonin (5-HT) and its receptors in the GI tract has also been investigated. While many 5-HT receptor subtypes (5-HT$_1$, 5-HT$_2$, 5-HT$_3$ and 5-HT$_4$) are known to play a role in enteric neuroregulation and perception, research and product development attention has focused, in particular, on the 5-HT$_3$ receptor, which is known to be present on substance-P containing afferent neurons within the gut (20-21). However, while there are several 5-HT$_3$ antagonists available, including ondansetron, which is an antiemetic, and granisetron, no such antagonist is currently approved by the United States Food and Drug Administration (FDA) for use in treating irritable bowel syndrome, although the FDA has approved Lotronex (alosetron hydrochloride), a potent serotonin 5-HT$_3$ antagonist, for use in the treatment for diarrhea-predominant irritable bowel syndrome (D-IBS) in women (22). However, after notifying the FDA of post-marketing reports that reported serious adverse events associated with Lotronex, Glaxo Wellcome withdrew Lotronex from the market.

Members of the class of 5-HT$_4$ receptor antagonists also has been studied in this capacity (23). In addition, other drugs being examined for their modulation of visceral sensitivity include: (i) the opioid kappa receptor agonists such as fedotozine, which, unlike agents which act on opioid mu and delta receptors located in the GI tract, does not appear to have undesirable central effects, and, (ii) the somatostatin analogues such as octreotide (24-25). Antidepressants, which have been used for a number of years to treat associated affective disorder in irritable bowel syndrome patients, may address the increased pain perception that many of these patients experience. In particular, the tricyclic antidepressants, which exert useful actions at several locations along the brain-gut axis, may mediate the increased pain perception in these individuals (26-27). Sigma 1 receptor (".sigma.1," "sigma," or "sigma 1") agonists have been shown to possess antidepressant and anxiolytic properties. In vitro and in vivo studies have demonstrated that sigma 1 sites are implicated in control of motor behavior, regulation of smooth muscle contraction, and control of gut secretions, specifically alkaline secretions, and, therefore, may alleviate the increased gut motility and increased gut secretions from which many irritable bowel syndrome patients suffer (28-30).

As can be seen by the discussion supra, the symptomologies of irritable bowel syndrome are caused by a complex pharmacology. Current treatment options for irritable bowel syndrome and/or related conditions do not adequately address the complexities of irritable bowel syndrome and therefore, current treatments remain inadequate or, as exemplified by the recent withdrawal from the United States market of the serotonin 5-HT$_3$ antagonist Lotronex (alosetron hydrochloride). A treatment that is effective in treating bowel disorders such as irritable bowel syndrome, without producing severe adverse effects, is therefore desired. More particularly, a treatment for bowel disorders such as irritable bowel syndrome that works via a plurality of pharmacological mechanisms, is desired; such a treatment may be the most efficacious solution to the treatment of irritable bowel syndrome. Novel treatment options that may address one or more of the multiple therapeutic targets associated with irritable bowel syndrome and related bowel disorders or alleviate one or more of the symptomologies of irritable bowel syndrome and the related bowel disorders as described above, are therefore is great demand currently.

The prior art is deficient in an effective treatment for irritable bowel syndrome. The present invention fulfills this longstanding need and desire in the art.

SUMMARY OF THE INVENTION

The present invention is provides a new treatment for irritable bowel syndrome. The precise pathophysiology of irritable bowel syndrome is not well understood. Nevertheless, there is a heightened sensitivity to visceral pain perception in irritable bowel syndrome, known as visceral hyperalgesia. This sensitization involves a reduction in the threshold and an increase in the gain of the transduction processes of primary afferent neurons as well as spinal and other central neurons. In the periphery, this may be attributable to a variety of mediators including monoamines (both catecholamines and indoleamines), substance P, and variety of cytokines and prostanoids including the E-type prostaglandins.

Even though evidence for inflammation may exist in irritable bowel syndrome, it is clearly different than a typical inflammatory disorder such as ulcerative colitis or Crohn's Disease. First, there is no evidence for tissue injury or destruction either at the macroscopic or microscopic level. Secondly, the major cell types that appear to be affected in irritable bowel syndrome are the muscle and nerves, as compared with Inflammatory Bowel Disease where the epithelium is a prominent and major target. Therefore, even if immunocompetent cells are contributing to the pathogenesis of irritable bowel syndrome, they are doing so by means that are not intuitively obvious and may involve mechanisms different than those in Inflammatory Bowel Disease.

The present invention is directed to a method of treatment of irritable bowel syndrome and related disorders. Accordingly, in one embodiment of the present invention, there is provided a method of treating an individual having irritable bowel syndrome or a related disorder, comprising the step of administering to the individual a pharmacologically effective dose of a luminally active anti-inflammatory or immunosuppressive compound with minimal or no systemic side effects.

In another embodiment of the present invention, there is provided a method of inhibiting the onset of symptoms of irritable bowel syndrome or a related disorder in an individual in need of such treatment, comprising the step of administering to the individual a pharmacologically effective dose of a luminally active anti-inflammatory or immunosuppressive compound with minimal or no systemic side effects.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 1A: Adult rats sensitized with 0.2% acetic acid instilled into the rectum on neonatal day 10 and tested at 6 weeks age. FIG. 1B: adult rats sensitized with 5% acetic acid at 8 weeks age and tested at 12 weeks.

DETAILED DESCRIPTION OF THE INVENTION

Figure 1A:
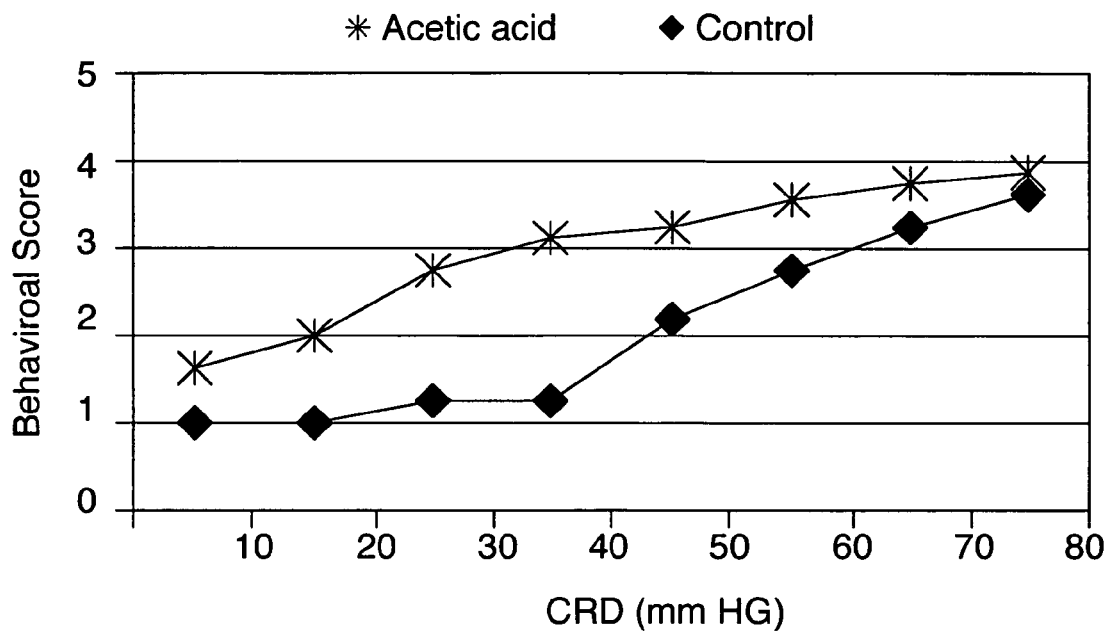
FIGS. 1A-1B show a behavioral response in response to colorectal distention.

The present invention discloses the use of luminally active anti-inflammatory or immunosuppressive compound with minimal or no systemic side effects that can be administered orally for the treatment of irritable bowel syndrome and related disorders. These compounds include steroids such as beclomethasone that are only minimally absorbed and others such as budesonide that though absorbed, undergo extensive first pass metabolism in the liver, and do not exert significant systemic effects. Other compounds useful for the treatment of irritable bowel syndrome would include anti-inflammatory and immunosuppressive agents that share the same features as above compounds, i.e., they are active in the lumen of the GI tract but do not exert systemic effects because of poor absorption or rapid metabolism by the liver before the reach the systemic circulation.

The target for these compounds is irritable bowel syndrome, a condition characterized by abdominal pain associated with a change in bowel movements. This syndrome has traditionally been considered a "functional" gastrointestinal disorder because of the lack of any obvious structural, morphological or histological changes. However, in recent years, there is increasing evidence to implicate a causative role for subtle inflammation in the form of infiltrating lymphocytes, mast cells and other immune-competent cells. This inflammation is mild enough that it can easily be missed on routine histological examination, but may be biologically significant enough to provide the basis for the altered bowel movements and pain that these patients experience. Accordingly, anti-inflammatory or immunosuppressive therapy is a logical approach to the treatment of these patients. However, traditional forms of these therapies are associated with significant systemic toxicity and may be difficult to justify for the treatment of what is a chronic, but generally benign syndrome. Anti-inflammatory agents that can be given orally but remain active only while in the lumen of the gastrointestinal tract are therefore ideal agents for the treatment of this syndrome.

A novel feature of the present methodology resides in the fact that irritable bowel syndrome has not been considered an inflammatory disorder. Even if irritable bowel syndrome is proven to be associated with significant inflammation, irritable bowel syndrome is distinct from inflammatory bowel disease (IBD) (typically Crohn's and ulcerative colitis) both in terms of pathophysiology and clinical approach.

The present methodology may also be used to treat disorders related to irritable bowel syndrome that affect the stomach (functional dyspepsia) and esophagus (noncardiac chest pain). NUD refers to non-ulcer dyspepsia, which in many surveys is the most common cause of upper gastrointestinal symptoms in the general population. Clinically, it may mimic peptic ulcer disease, delayed gastric emptying or even gastroesophageal reflux but no evidence of these is found on diagnostic testing. NCCP or noncardiac chest pain, is a syndrome of unexplained chest pain that may mimic an acute coronary event but no evidence of cardiac disease can be found. It is present in as many as 50-75% of patients presenting to the emergency room with acute chest pain. Current thinking attributes these symptoms to generating from the esophagus.

Like irritable bowel syndrome, both non-ulcer dyspepsia and noncardiac chest pain are categorized as functional gastrointestinal disorders, i.e., collections of symptoms attributable to the gastrointestinal tract in the absence of mucosal, structural, or biochemical disease. They have common etiopathogenetic features, notably psychosocial disturbances, dysmotility, heightened sensitivity, and, possibly, an association with a postinfective or postinflammatory state. Like irritable bowel syndrome, the pathophysiology of these conditions has been poorly characterised and the optimum treatment remains uncertain.

Thus, in accordance with the description above, the present invention is directed towards a method of treating an individual having irritable bowel syndrome or a related disorder, comprising the step of administering to said individual a pharmacologically effective dose of a luminally active anti-inflammatory or immunosuppressive compound with minimal or no systemic side effects. In one aspect of this embodiment, the minimally-absorbable, luminally active anti-inflammatory compound is a steroid. One preferred steroid is beclomethasone in the form of beclomethasone dipropionate. In a preferred embodiment, the beclomethasone dipropionate is DOR Biopharma's orBec™. The orBec™ formulation allows for larger doses of beclomethasone dipropionate to be delivered to the afflicted area without systemic side effects associated with other steroids because of intestinal hydrolysis of the propionate residues, high first-pass effect conversion to beclomethasone (a weak steroid), incomplete absorption and rapid deactivation of the most active steroid by the hepatic metabolism. Typically, the orBec™ is administered in a dose of from about 0.1 mg/kg to about 20 mg/kg. In a more preferred embodiment, orBec™ is administered in a dose of from about 1 mg/d to about 3 mg/d.

In one aspect of this embodiment, the luminally active anti-inflammatory compound with minimal or no systemic side effects is budesonide. Alternatively, other compounds such as clobetasol, halbetasol, fluocinonide, halcinonide, betamethasone, mometisone, alclometasone, triamcinolone or fluocinolone may be used.

Alternatively, an immunosuppressive compound such as methotrexate, azothiorpine, 6 mercaptopurine, cyclosporine and FK506 may be used in the methods of the present invention.

The compounds described above may be used to treat or prevent not only irritable bowel syndrome but also related disorders such as non-ulcer dyspepsia or noncardiac chest pain.

In another embodiment, the present invention is directed towards a method of inhibiting the onset of symptoms of irritable bowel syndrome or a related disorder in an individual in need of such treatment, comprising the step of administering to the individual a prophylactically effective dose of a luminally active anti-inflammatory or immunosuppressive compound with minimal or no systemic side effects. The compounds useful in preventing or inhibiting the onset of symptoms of irritable bowel syndrome or a related disorder are described above with respect to treatment of these disorders.

EXAMPLE 1

Effect of Oral Beclamethasone Dipropionate (BDP) on Acetic Acid Sensitized Rats

Figure 1B:
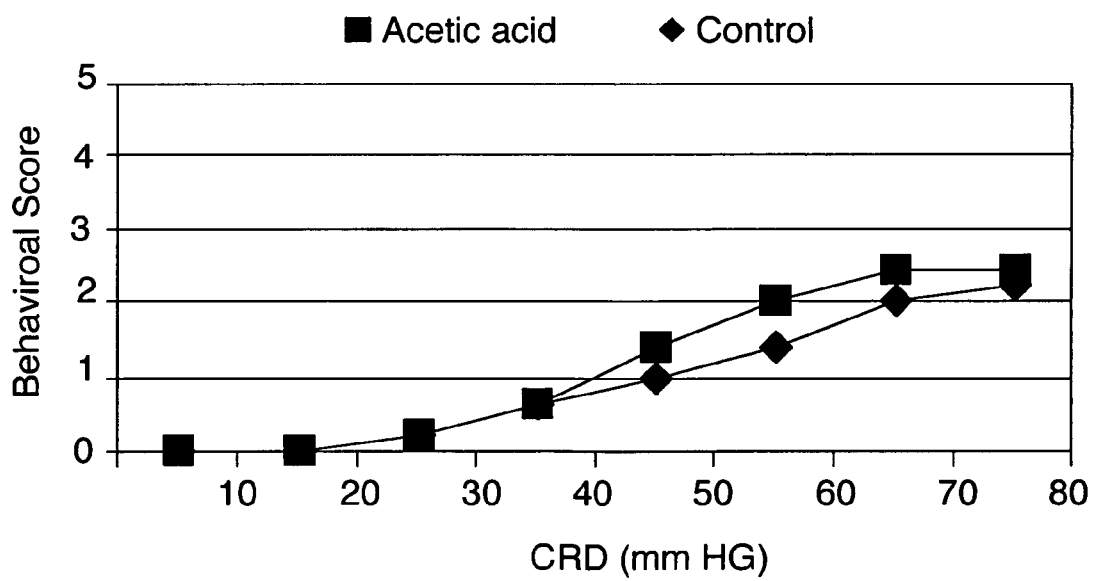

Neonatal sensitization with acetic acid: Description of the model. It was previously shown that transient noxious stimulation of the colon during postnatal development can cause long-lasting hyperalgesia, despite complete resolution of the initiating event. In a variation of this technique, 0.3% acetic acid was instilled into the rectum of rats at postnatal days 7-10. This results in sustained hyperalgesia and allodynia to graded colorectal distention as measured between weeks 4-12, using both behavioral assays and visceromotor reflexes (using EMG recordings from the anterior oblique muscle) (FIG. 1A). By contrast, when rats are treated with acetic acid as adults, and tested after a similar period of time, no sensitization is observed (FIG. 1B).

Sprague Dawley rat pups were sensitized on neonatal day 10 with acetic acid. In brief, a thin polyethylene tubing (P-90) was introduced gently into the rectum 2 cm from the anus. 0.2 ml of 0.5% glacial acetic acid in normal saline was injected through the tube into the colo rectum. The pups were allowed to grow into adults. When the rats were approximately eight weeks old they were weighed and their behavioral responses to graded (10 mm-80 mm Hg) colo rectal distention (CRD) was determined (FIG. 1B).

Colo Rectal Distention (CRD):

Under light brevital (1%) anesthesia a polyethelene tube connected to a balloon (made out of a glove finger) was guided into the colo-rectum ~8 cms from the rectum and the tube was fastened to the tail. The open end was connected to the barostat device. The rat was put into a rat restrainer allowing limited movement. After the rat was acclimatized to the restrainer (half an hour) the colon was distended (between 10 mm-80 mm Hg) for 20 seconds with a rest period of 2 minutes and their behavioral response grading was noted. 0=normal, 1=abdominal contractions, 2=lifting of abdominal wall and 3=body arching and lifting of pelvic structure.

Oral BDP Treatment

Figure 2A:
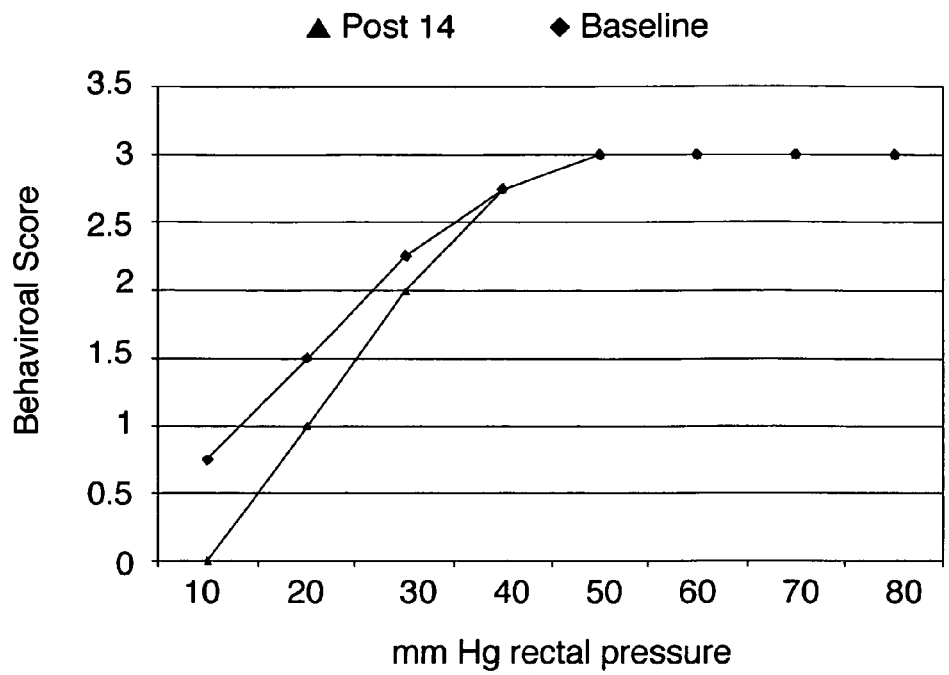
FIGS. 2A-2B shows that beclamethasone dipropionate treated rats showed higher pain threshold to graded CRD (FIG. 2A) compared to the vehicle treated group (FIG. 2B).
Figure 2B:
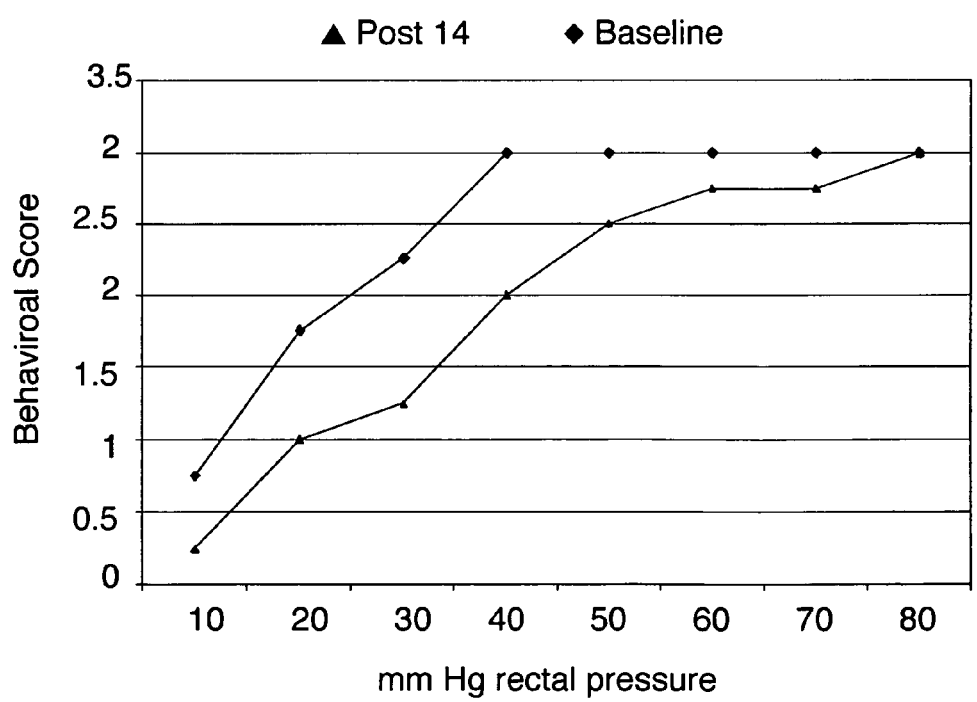

The sensitized rats were orally fed with beclamethasone dipropionate dissolved in corn oil (1.5 mg/kg body weight) daily for two weeks. Control group received equal volume of the vehicle (corn oil). After two weeks the rats were again tested for their behavioral response to graded CRD. As shown in FIGS. 2A-2B, beclamethasone dipropionate treated rats (FIG. 2A) showed higher pain threshold to graded CRD compared to the vehicle treated group (FIG. 2B).

The following references are cited herein.
1. Malcolm A. and Kellow J. E. MJA, 1998, 169:274-279.
2. Collins et al., Can J Gastroenterol, 1999, 13A:47A-49A.
3. Collins et al. Baillieres Best Pract Res Clin Gastroenterol, 1999, 13:429-436.
4. Mayer et al. Gastroenterology, 1994, 107:271-293.
5. Kellow et al. Gastroenterlogy, 1987, 92:1885-1893;
6. Levitt et al. Ann Int Med, 1996, 124:422-4.
7. Drossman et al. Gastroenterlogy Int, 1995, 8:47-90.
8. Efskind et al. Scand J Gastroenterol, 1996, 31:463-8.
9. Lucy et al. Gut 1987, 28:221-25;
10. Frances C. Y. and Whorwell P. J. Lancet, 1994, 34:496-500.
11. Shutze et al. Aliment Pharmacol Ther, 1997, 1(1):387-94.
12. Klein, K. B. Gastroenterology, 1988, 95:232-241.
13. Poynard et al. Aliment Pharmacol Ther, 1994, 8:499-510.
14. DePonti et al. Pharmacol Ther, 1996, 69:59-78;
15. Tonini M. Pharmacol Res, 1996, 33:216-26;
16. Mathias et al. Dig Dis Sci, 1994, 39:1155-62;
17. Wettstein et al. Pharmacol Ther, 1994, 62:267-82;
18. Evans et al., Gastroenterology, 1994; 106:A495.
19. DePonti et al., Br J Pharmacol, 1995, 1(14):1447-1453.
20. Farthing M G: Scand J Gastroenterol, 1991, 26:92-100.
21. Galligan J. J. Electrophysiological studies of 5-hydroxytriptamine receptors on enteric neurons" In: Serotonin and Gastrointestinal Function pp 109-126, Gaginella T S and Galligan J J (eds.) CRC Press, Boca Raton.
22. Mangel A. W. and Northcutt A. R. Aliment Pharmacol Ther, 1999, 13 Suppl. 2:77-82.
23. Houghton et al., Gut, 1997, 4Suppl. 3:A26.
24. Junien J L and Riviere P. Aliment Pharmacol Ther, 1995, 9:117-26.
25. Halser et al., Gastroenterology, 1993, 104:1390-7.
26. Gorard et al., Dig Dis Sci, 1995, 40:86-95.
27. Peghini et al., Gastroenterology, 1997, 1(12):A255.
28. Walker et al., Neurology, 1988, 38:961-965.
29. Vaupel et al., Eur J Pharmacol, 1987, 139; 125-128.
30. Campbell et al., Eur J Pharmacol, 1987, 138; 447-449.

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for treating irritable bowel syndrome in an individual suffering from the same, comprising: administering to the individual a dose of a luminally-active steroid that is pharmacologically effective to reduce visceral hyperalgesia and allodynia in the individual, thereby treating the irritable bowel syndrome.

2. The method of claim 1, wherein the luminally-active steroid is budesonide, clobetasol, halbetasol, fluocinonide, halcinonide, betamethasone, mometisone, alclometasone, triamcinolone, or fluocinolone.

3. The method of claim 1, wherein the dose is administered orally.

* * * * *